United States Patent [19]

Thompson

[11] Patent Number: 5,339,831

[45] Date of Patent: Aug. 23, 1994

[54] POUCH WITHIN A POUCH DESIGN

[75] Inventor: Joseph F. Thompson, Lindenhurst, Ill.

[73] Assignee: Baxter International Inc., Deerfield, Ill.

[21] Appl. No.: 828,378

[22] Filed: Jan. 30, 1992

[51] Int. Cl.⁵ ............................................. A61F 13/00
[52] U.S. Cl. ................................. 128/852; 128/849
[58] Field of Search ................................. 128/849–856

[56] References Cited

U.S. PATENT DOCUMENTS

| Re. 27,710 | 7/1973 | Melges . | |
| 4,051,845 | 10/1977 | Collins | 128/855 |
| 4,076,017 | 2/1978 | Haswell . | |
| 4,089,331 | 5/1978 | Hartigan et al. . | |
| 4,105,019 | 8/1978 | Haswell | 128/849 X |
| 4,476,860 | 10/1984 | Collins et al. . | |
| 4,570,628 | 2/1986 | Neal . | |
| 4,596,245 | 6/1986 | Morris | 128/852 |
| 4,730,609 | 3/1988 | McConnell . | |
| 4,957,120 | 9/1990 | Grier-Idris | 128/849 |
| 5,010,899 | 4/1991 | Thompson | 128/849 |
| 5,038,798 | 8/1991 | Dowdy et al. | 128/849 X |
| 5,074,316 | 12/1991 | Dowdy | 128/849 |
| 5,095,918 | 3/1992 | Busch | 128/849 |
| 5,107,859 | 4/1992 | Alcorn et al. | 128/849 X |

Primary Examiner—Robert A. Hafer
Assistant Examiner—Sam Rimell
Attorney, Agent, or Firm—Kay H. P. Hannafan; Paul C. Flattery

[57] ABSTRACT

A double pouch is described in which a smaller pouch is located within a larger pouch. The larger pouch can be used to accommodate a patient's leg or other appendage during a surgical procedure while the smaller pouch can be used to retain irrigation fluids and surgical debris. In the preferred embodiment, the smaller pouch can be moved to the outside of the larger pouch when the larger pouch is not intended to be used. In one embodiment, the pouches can be attached to a main drape having a fenestration through which a patient's appendage is inserted.

19 Claims, 6 Drawing Sheets

POUCH WITHIN A POUCH DESIGN

BACKGROUND OF THE INVENTION

1. Field of the Invention

The invention relates generally to surgical drapes for procedures in which a patient's appendage is being operated on and more specifically to surgical drapes for use in hip replacement procedures.

2. Brief Description of the Prior Art

In surgical procedures, it is usually necessary to drape a portion of a patient's body and to leave another portion of the patient's body exposed. A major reason for draping a patient's body is to prevent infection by providing a sterile field around the operative site. In a hip replacement procedure, it is generally desirable to drape the patient's entire body leaving only the hip area exposed. Several drapes have been designed to accomplish this purpose. For example, U.S. Pat. No. 4,730,609 to McConnell describes a surgical drape having a fenestration for the hip area through which a patient's leg is inserted. The patient's leg is then covered with a boot made from a conformable impervious material. The boot has a tubular side wall which is joined to the main sheet of the drape. One disadvantage of a drape of this type is that it may be difficult to insert the patient's leg through the boot of the drape. Thus, a need exists to provide a drape which is easier to arrange over the patient's leg and is more versatile with regard to positioning of the patient.

Another surgical drape used in hip replacement procedures is s described in U.S. Pat. No. 4,957,120 to Grier-Idris. This drape includes a main sheet having a fenestration through which a patient's leg is inserted. To one side of the fenestration is a pocket which is generally attached on three sides to the main sheet of the drape and which includes an opening on the fourth side, adjacent the fenestration, into which a patient's leg can be inserted. While this drape provides much needed versatility and ease in placement of a patient's appendage, one disadvantage of the drape is that any fluids, surgical instruments or surgical debris can easily enter into the pocket. This can be cumbersome during a surgical procedure in which large amounts of irrigation fluids are used or whenever sponges or other surgical instruments are inadvertently dropped into the pocket of the drape. Large amounts of irrigation fluid can weigh down the drape and keep the patient's appendage undesirably moist. Any surgical sponges or other medical instruments which drop into the pocket must be removed prior to the completion of the surgical procedure for counting in order to ensure that they have not been left in a patient.

Another disadvantage of a pocket of the type described in U.S. Pat. No. 4,957,120 is that the lower portion of the pocket is attached to the main sheet of the surgical drape. This means that if it is desired to elevate a patient's leg during the surgical procedure, the entire drape in the vicinity of the pocket will be raised. This can undesirably compromise the sterility of the surgical field. Even if the sterility of the surgical field is not compromised, the attachment of the lower portion of the pocket to the main drape reduces the mobility of the patient's appendage. Mobility of a patient's leg during a hip replacement procedure is important because a surgeon will frequently wish to manipulate a patient's leg during the surgical procedure to allow the insertion of the prosthetic hip and ensure that the prosthesis is functioning properly.

Another disadvantage of the drape described in U.S. Pat. No. 4,957,120 is that the main sheet of the drape and the pocket are permanently attached to one another along at least a portion of the periphery of the pocket. Thus, it is not possible to use the pocket with a simple drape having only a fenestration or with a pair of U-shaped drapes. Such drapes are preferred by some surgeons during a hip replacement procedure. Therefore, a need existed to be able to provide a pocket for accommodating a patient's leg when such drapes are used.

It is therefore an object of the present invention to provide a device for accommodating a patient's leg during a hip replacement procedure in which the device also includes a means for retaining irrigation fluid, surgical instruments, and surgical debris in a separate pouch.

It is also an object of the present invention to provide a flexible device which can be removably attached to one or both sides of a fenestration on the main sheet of a surgical drape in which a first big pouch can be used to accommodate a patient's leg and a second smaller pouch can be used to retain irrigation fluids, surgical instruments and surgical debris. Specifically, it is also an object of the invention to be able to close off the opening of the big pouch when it is not being used while still being able to control and retain irrigation fluids and the like.

Still yet another object of the subject invention is to provide a surgical drape having a big pocket for accommodating a patient's leg in which the leg and pocket can be manipulated without manipulating the portion of the main sheet of the drape that underlies the big pocket.

Another object of the subject invention is to provide a smaller fluid-retaining pocket inside a big pocket in which the openings of each pocket can be releasably attached to one another and in which one or more of the openings are provided with a stiffening means to enhance the placement of the pockets with respect to a patient's leg.

SUMMARY OF THE INVENTION

The invention can be briefly described as a device for covering a patient's appendage during a surgical procedure. The device includes a big pouch having an upper sheet and a lower sheet. Both the upper and the lower sheets have at least a first and a second peripheral section. The first peripheral sections of each sheet are generally attached to one another. The second peripheral sections of each sheet are generally unattached to one another and define a big opening. A patient's leg or other appendage may be inserted into the big pouch through the big opening between the second peripheral sections of the upper and the lower sheets. The big pouch is generally large enough to accommodate, or hold, an entire leg or other appendage.

The device also includes a smaller pouch which also has an upper and lower sheet. Both the upper and lower sheets of the smaller pouch also have at least a first and a second peripheral section. The first peripheral sections of each sheet of the smaller pouch are generally attached to one another. The second peripheral sections of each sheet of the smaller pouch are generally unattached to one another to define a smaller opening relative to the big opening of the big pouch.

In the preferred embodiment the second peripheral section of the lower sheet of the big and smaller pouches are connected to one is another. The smaller pouch is moveable from a first position to a second position relative to the big pouch. In the first position, the smaller opening of the smaller pouch is located immediately within the big opening of the big pouch and the smaller pouch is generally located entirely within the big pouch. In the second position, the second peripheral section of the lower surface of the smaller pouch overlies the big opening of the big pouch, effectively closing the big opening. In the second position, the smaller pouch is generally located entirely outside of the big pouch.

DETAILED DESCRIPTION OF THE PREFERRED EMBODIMENT

A device 10 for covering a patient's appendage during a surgical procedure is described. The device includes a big pouch 12 having an upper sheet 14 and a lower sheet 16 (see FIG. 2). The upper and lower sheets 14,16 each have a first and a second peripheral section 18,20, respectively. The first peripheral section 18 of each of the upper and lower sheets 14,16 are generally attached to one another. The second peripheral sections of each sheet are generally unattached to one another to define a big opening 22 and to allow a patient's appendage to be inserted into the big pouch 12 between the second peripheral sections 20. In the preferred embodiment, the big pouch 12 is large enough to accommodate the entire appendage of a patient.

While the big pouch 12 has been described as having upper and lower sheets 14,16, it is not necessary for these sheets to be entirely separate sheets. For example, the upper and lower sheets 14,16 may be formed from a single, integral piece of material 24 which has been folded to form the lower portion of the big pouch 12. Alternatively, the big pouch can be formed of two separate sheets of material which are sealed onto one another about the first peripheral section 18. Although the big pouch 12 has been illustrated as a rectangularly shaped pouch, other shapes may be used, such as semicircular, triangular, or polygonal shapes.

The device 10 also includes a smaller pouch 26 having an upper and lower sheet 28,30, respectively. The upper and lower sheets 28,30 of the smaller pouch 26 each have at least a first and a second peripheral section 32,34. The first peripheral sections 32 of each sheet 28,30 of the smaller pouch 26 are generally attached to one another. The second peripheral sections 34 of each sheet 28,30 of the smaller pouch 26 are generally unattached to one another to define a smaller opening 36 relative to the big opening 22 of the big pouch 12.

Figure 2:
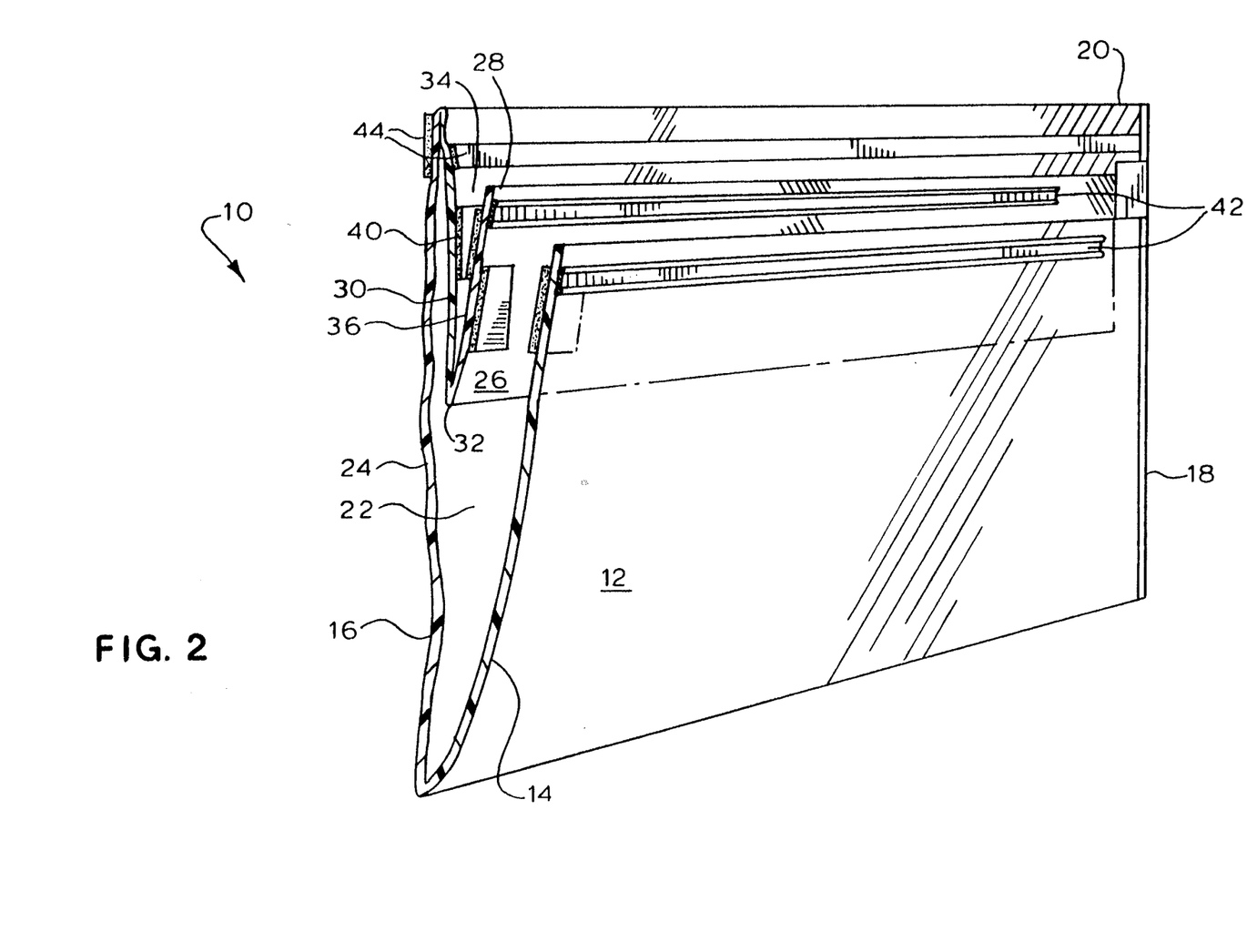
FIG. 2 is a side, cut-away view of the embodiment illustrated in FIG. 1.
Figure 3:
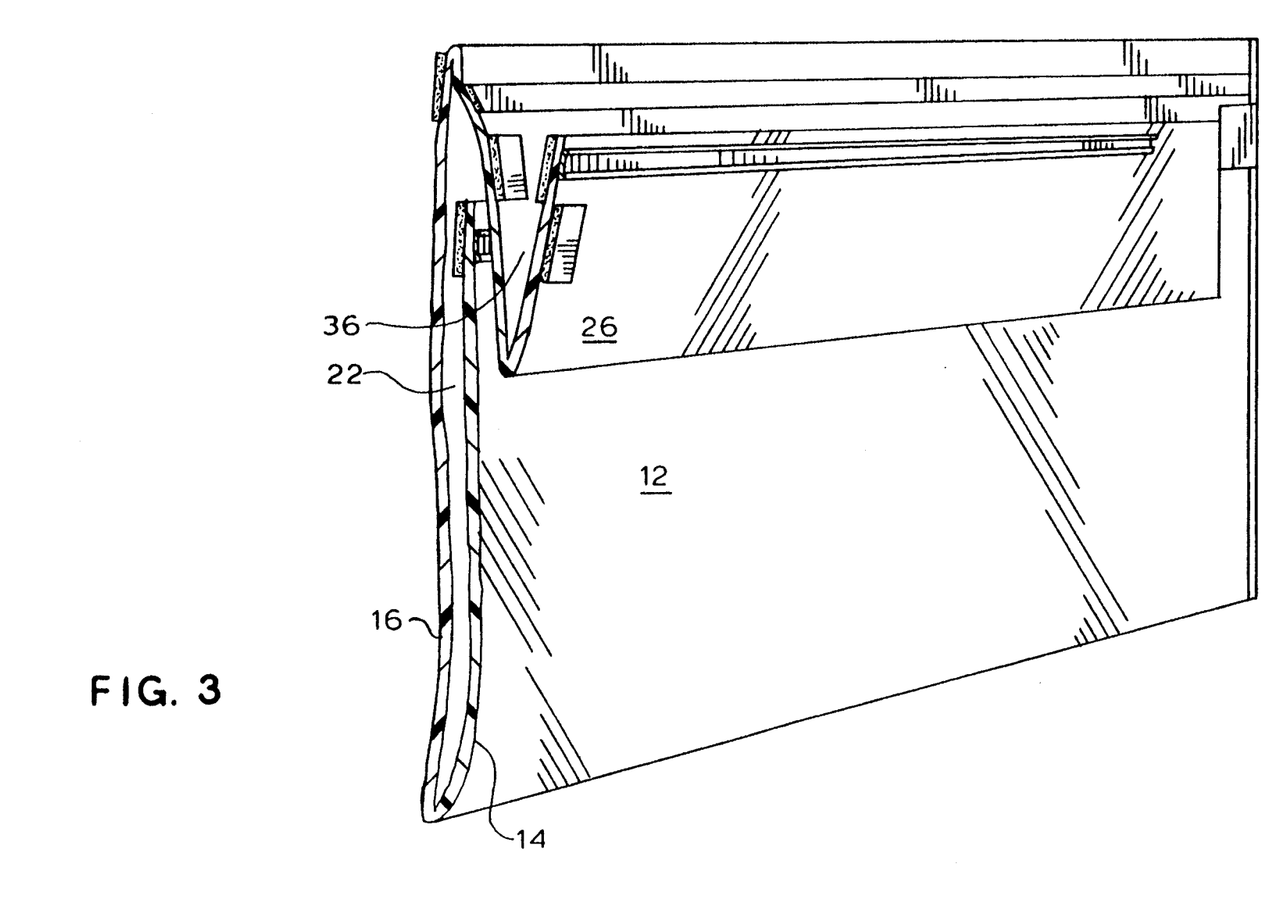
FIG. 3 is a side, cut-away view of one embodiment of the invention in which the smaller pouch is in the second position.

The second peripheral sections 20,34 of the lower sheets 16,30 of each of the big and smaller pouches 12,26 are connected to one another. This connection causes the big opening 22 and the smaller opening 36 to be in parallel juxtaposition with one another. In the preferred embodiment, the smaller pouch 26 is moveable from a first position as illustrated in FIG. 2 to a second position which is illustrated in FIG. 3. In the first position, the smaller opening 36 of the smaller pouch 26 is located immediately within the big opening 22 of the big pouch 12. Thus, the smaller pouch 26 is generally located entirely within the big pouch 12.

In the second position, the second peripheral section 34 of the lower sheet 30 of the smaller pouch 26 overlies the big opening 22. Thus, as illustrated in FIG. 3, in the second position the smaller pouch 26 is generally located outside the big pouch 12.

In the preferred embodiment, both the big pouch 12 and the smaller pouch 26 are made from transparent materials. A preferred material is polyethylene. Other polyesters or polyolefins may be used in alternative embodiments. A transparent material is preferred because it allows medical personnel to view the patient's appendage and any other objects which may be located in the pouches during the surgical procedure.

Figure 1:
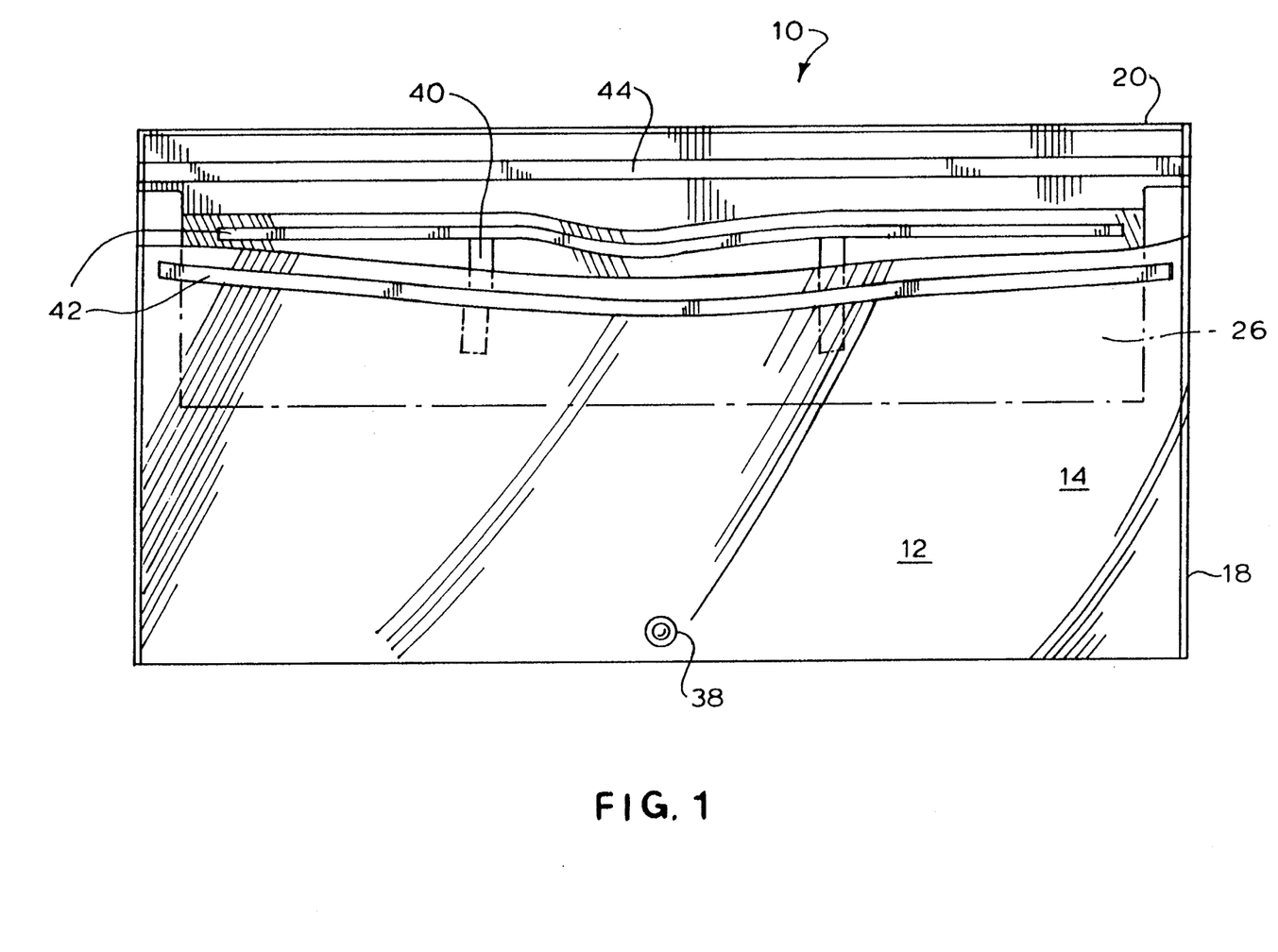
FIG. 1 is a perspective view of one embodiment of the invention.

In a preferred embodiment of the invention, the first and second peripheral sections 32,34 of the smaller pouch 26 are generally smaller than the first and second peripheral sections 18,20 of the big pouch 12 so that the smaller pouch 26 can lie flat within the big pouch 12 when the pouches 12,26 are in the first position. This is illustrated in both FIGS. 1 and 2.

In one embodiment of the invention, the big pouch 12 includes at least one drainage port 38. This port may be located in a variety of positions along the first peripheral section 18 of the big pouch 12.

In a preferred embodiment of the invention, both the big pouch 12 and the smaller pouch 26 include a means 40 for releasably attaching the second peripheral sections 20,34 of the upper sheets 14,28 of the big and smaller pouches 12,26 to one another. Generally, in the preferred embodiment, this means for releasably attaching 40 is accomplished through the use of a "hook-and-loop" fastener. The use of a means for releasably attaching 40 the upper sheets 14,28 to one another allows the device to be more easily handled without the smaller opening 36 or the big opening 22 producing undesirable gaps as the subject device 10 is handled. In the preferred embodiment, the second peripheral sections 34 of the upper and lower sheets 28,30 are also provided with a means 40 for releasably attaching the sheets to one another.

In another embodiment of the subject invention, the device 10 further includes a means 42 for stiffening the second peripheral sections 20,34 of the upper sheets 14,28 of at least one of the big and smaller pouches 12,26. The purpose of the stiffening means 42 is to allow medical personnel to shape either the big or small opening 22,36 about a patient's appendage or to shape the openings to produce a desired gap to allow fluids or other materials to enter the smaller pouch 26. Various stiffening means 42 can be used. In the preferred embodiment, polymer coated wires are sealed to the upper sheets 14,28 along the second periphery sections 20,34.

In one embodiment of the invention, a means 44 for attaching the second peripheral section 20 of the lower sheet 16 of the big pouch 12 to a surface adjacent a patient's appendage. For instance, the attachments means 44 can be used to attach the big pouch 12 to a plain drape, a table surface, or even a portion of the patient.

Figure 4:
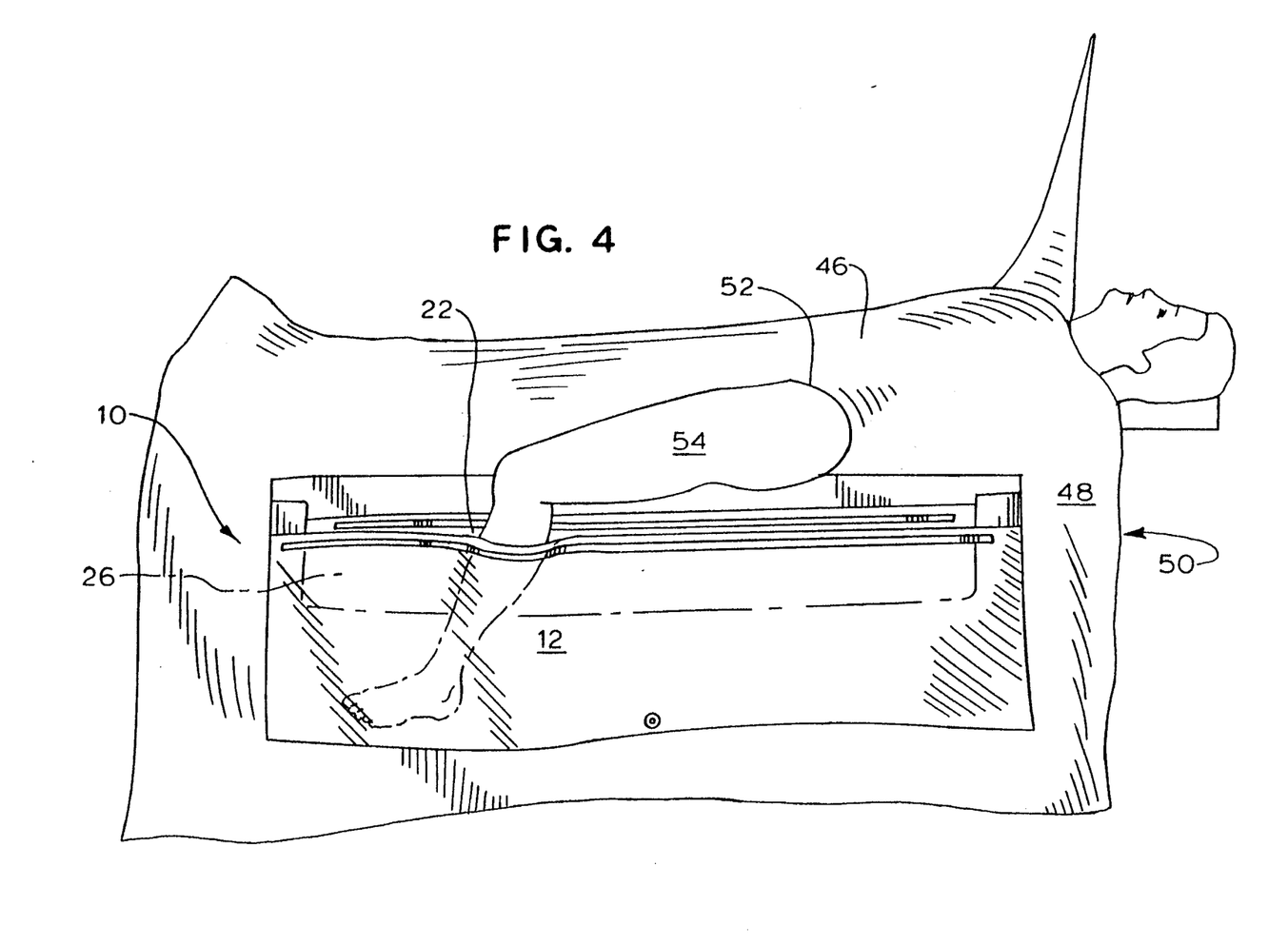
FIG. 4 is a perspective view of one embodiment of the invention in which the big and smaller pouches are attached to the main sheet of a drape.

In a preferred embodiment of the invention, the device 10 is attached to a main surgical drape 46 having an upper and lower surface 48,50, respectively, as illustrated in FIG. 4. The main drape 46 includes a fenestration 52 in the preferred embodiment of the invention through which a patient's appendage 54 may be inserted. The device 10 is generally attached to one side of the fenestration 52 and the patient's appendage 54 may be inserted through the big opening 22 into the big pouch 12. In the preferred embodiment, the smaller pouch 26 is located within the big pouch 12 and underneath the patient's appendage 54. The smaller pouch 26 collects irrigation fluids, medical sponges, and other surgical debris during a surgical procedure which otherwise might undesirably fall into the big pouch 12.

Figure 5:
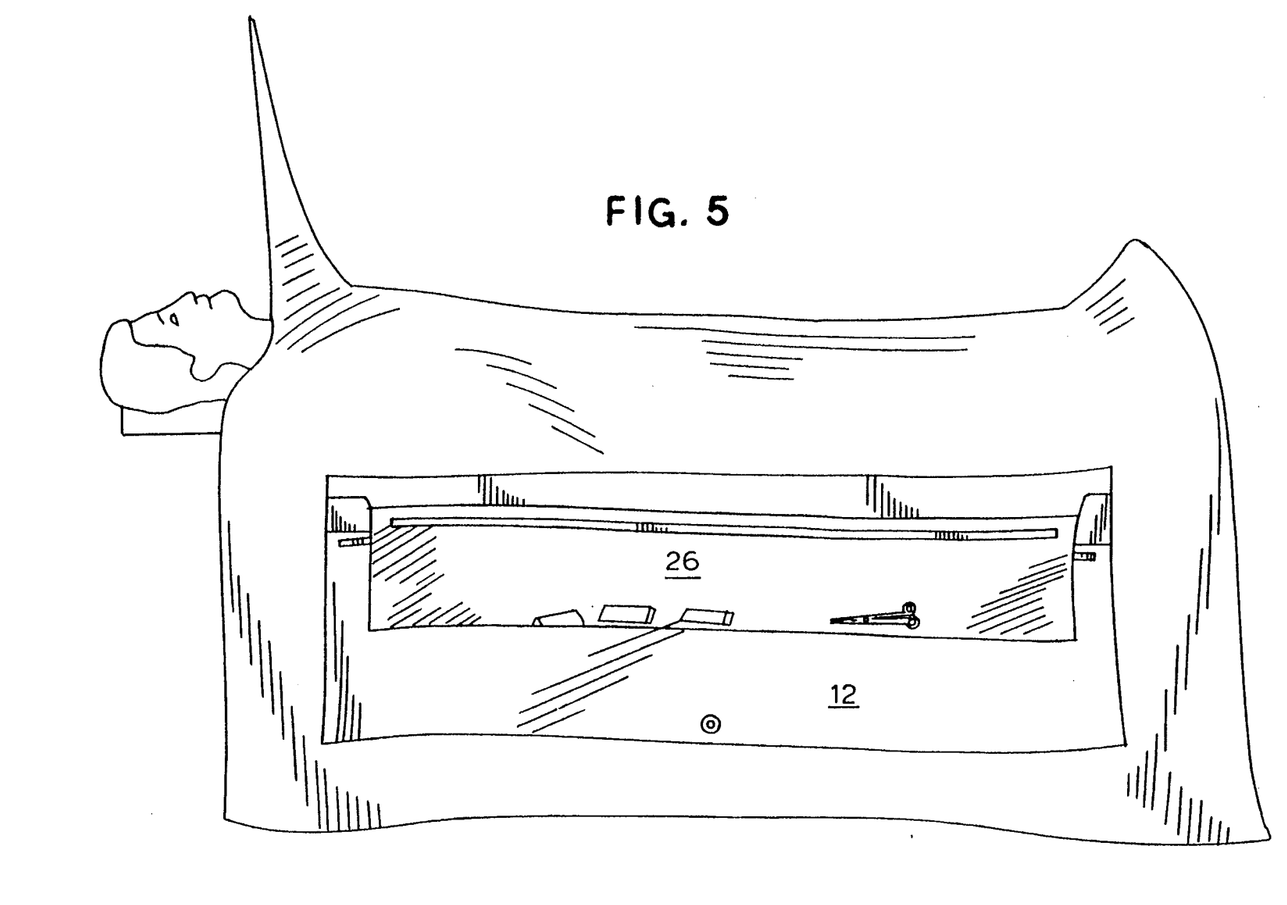
FIG. 5 is a perspective view of another embodiment of the invention in which the big and smaller pouches are attached to the main sheet of a drape and the big pouch is not in use.
Figure 6:
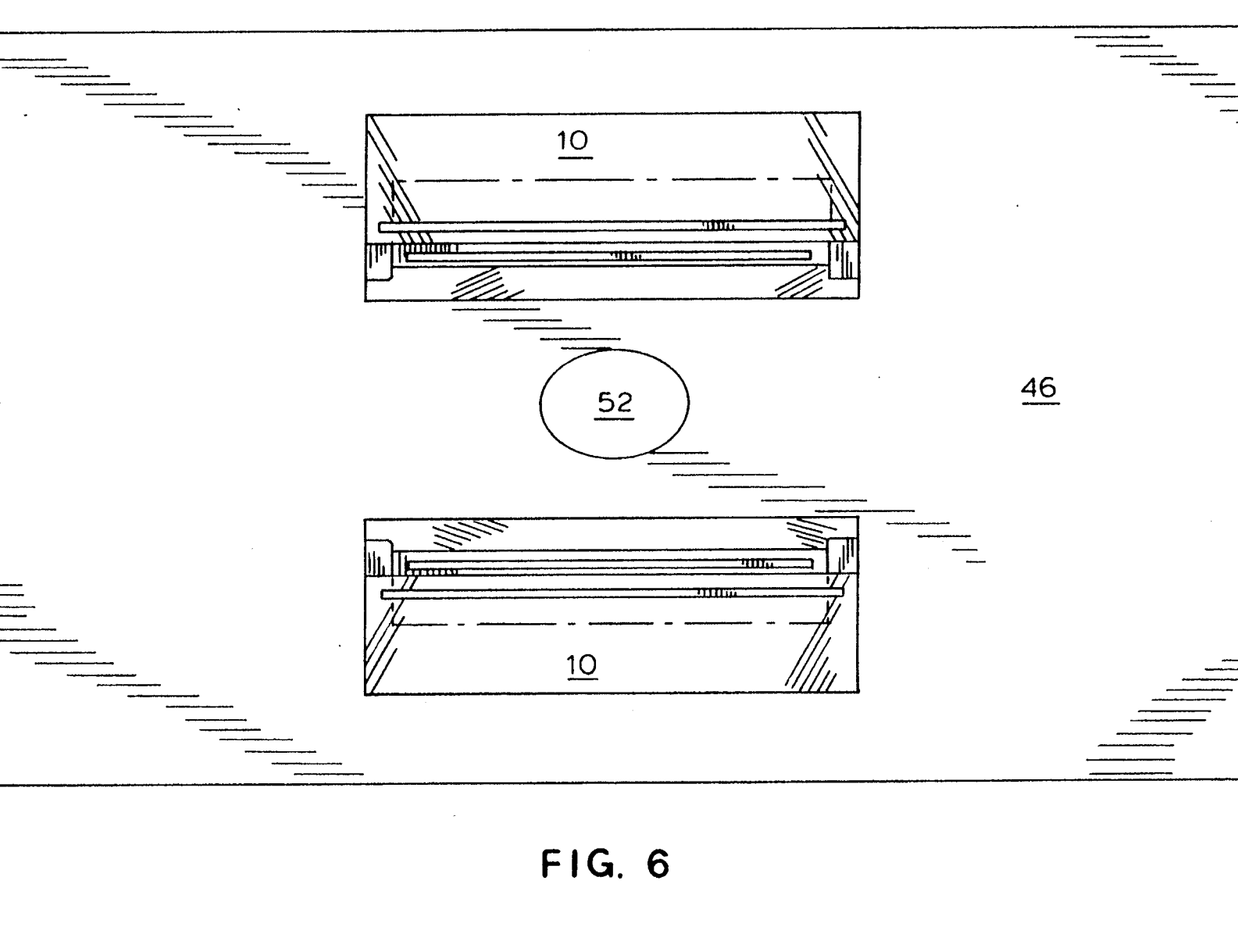
FIG. 6 is a top view of one embodiment of the invention in which two pairs of pouches are attached to the main sheet of a drape on opposite sides of a fenestration.

As illustrated in FIG. 6, in a preferred embodiment of the invention, a device 10 as described above is attached to opposite sides of a fenestration 52 of a main drape 46. Thus, the same drape can be used to perform a surgical procedure on either the right or left appendage of a patient. The big pouch 12 that is in use as illustrated in FIG. 4 has the smaller pouch 26 located in the first position. The big pouch 12 that is not in use as illustrated in FIG. 5 has the smaller pouch 26 located in the second position, thereby effectively closing the big opening 22 of the big pouch 12. Thus, it is possible to provide a relatively simple drape which is flexible in that it can be used for surgical procedures on either a left or right appendage and has a relatively simple way of closing a big pouch 12 on the unused portion of the drape.

One important feature of the preferred embodiment of the invention is that the device 10 is attached to the upper surface 48 only along the second peripheral section 20 of the big pouch 12. This allows the first peripheral section 18 of the big pouch 12 to be free from the upper surface 48 of the main surgical drape 46. This is very important because it allows a surgeon to easily manipulate a patient's appendage 54 during a surgical procedure without having to move portions of the drape 46 that are adjacent to the first peripheral section 18 of the big pouch 12.

While the invention has been described in detail and with reference to specific embodiments thereof, it will be apparent to those skilled in the art that various changes and modifications can be made therein without departing from the spirit and scope of the invention.

I claim:

1. A device for covering a patient's appendage during a surgical procedure, comprising:
    a big pouch having an upper sheet and a lower sheet, said upper and lower sheets each having at least a first and a second peripheral section, said first peripheral sections of each sheet being generally attached to one another about their periphery, and said second peripheral sections of each sheet being generally unattached to one another to define a big opening and to allow a patient's appendage to be inserted into said big pouch between said second peripheral sections, said big pouch being large enough to accommodate a patient's appendage;
    a smaller pouch also having an upper sheet and a lower sheet, said upper and lower sheets of said smaller pouch each having at least a first and a second peripheral section, said first peripheral sections of each sheet of said smaller pouch being generally attached to one another about their periphery, and said second peripheral sections of each sheet of said smaller pouch being generally unattached to one another to define a smaller opening relative to said big opening of said big pouch;
    said second peripheral section of said lower sheet of each of said big and smaller pouches being connected to one another,
    said smaller pouch being movable from a first position to a second position in which
        in said first position, said smaller opening of said smaller pouch is located immediately within said big opening of said big pouch and said smaller pouch is generally located within said big pouch, and
        in said second position, said second peripheral section of said lower sheet of said smaller pouch overlies said big opening, and said smaller pouch is generally located outside of said big pouch.
2. A device as recited in claim 1, wherein:
    said first and second sheets of said big and smaller pouches are transparent.
3. A device as recited in claim 1, wherein:
    said first and second peripheral sections of said smaller pouch are generally smaller than said peripheral sections of said big pouch so that said smaller pouch can lie flat within said big pouch when said pouches are in said first position.
4. A device as recited in claim 1, wherein:
    said big pouch includes a drainage port.
5. A device as recited in claim 1, further comprising:
    means for releasably attaching said second peripheral sections of said upper sheets of said big and smaller pouches to one another.
6. A device as recited in claim 1, further comprising:
    means for releasably attaching said second peripheral sections of said upper and lower sheets of said smaller pouch to one another.
7. A device as recited in claim 5, further comprising:
    means for releasably attaching said second peripheral sections of said upper and lower surfaces of said smaller pouch to one another.
8. A device as recited in claim 6, further comprising:
    means for stiffening said second peripheral sections of said upper sheet of at least one of said big and smaller pouches.
9. A device as recited in claim 1, further comprising:
    means for attaching said second peripheral section of said lower sheet of said big pouch to a surface adjacent a patient's appendage.
10. A surgical drape for use when operating on a patient's appendage, comprising:
    a main drape having an upper and lower surface, said main drape having a fenestration through which a patient's appendage may be inserted;
    a first big pouch having an upper sheet and a lower sheet, said upper and lower sheets each having at least a first and a second peripheral section, said first peripheral sections of each sheet being generally attached to one another about their periphery, and said second peripheral sections of each sheet being generally unattached to one another to define a first big opening and to allow a patient's appendage to be inserted into said first big pouch between said second peripheral sections, said first big pouch being large enough to accommodate a patient's appendage; said second peripheral section of said lower sheet of said first big pouch being attached to said upper surface of said main drape on a first side of said fenestration;

a first smaller pouch also having an upper sheet and a lower sheet, said upper and lower sheets of said first smaller pouch each having at least a first and a second peripheral section, said first peripheral sections of each sheet of said first smaller pouch being generally attached to one another about their periphery, and said second peripheral sections of each sheet of said first smaller pouch being generally unattached to one another to define a first smaller opening relative to said first big opening of said first big pouch;

said second peripheral section of said lower sheet of each of said first big and first smaller pouches being connected to one another, said first smaller pouch being movable from a first position to a second position in which in said first position, said first smaller opening of said first smaller pouch is located immediately within said first big opening of said first big pouch and said first smaller pouch is generally located within said first big pouch, and in said second position, said second peripheral section of said lower surface of said first smaller pouch overlies said first big opening, and said first smaller pouch is generally located outside of said first big pouch.

11. A surgical drape as recited in claim 10, further comprising: a second big pouch having an upper sheet and a lower sheet, said upper and lower sheets each having at least a first and a second peripheral section, said first peripheral sections of each sheet being generally attached to one another about their periphery, and said second peripheral sections of each sheet being generally unattached to one another to define a second big opening and to allow a patient's appendage to be inserted into said second big pouch between said second peripheral sections, said second big pouch being large enough to accommodate a patient's appendage; said second peripheral section of said lower sheet of said second big pouch being attached to said upper surface of said main drape on a second side of said fenestration;

a second smaller pouch also having an upper sheet and a lower sheet, said upper and lower sheets of said second smaller pouch each having at least a first and a second peripheral section, said first peripheral sections of each sheet of said second smaller pouch being generally attached to one another about their periphery, and said second peripheral sections of each sheet of said second smaller pouch being generally unattached to one another to define a second smaller opening relative to said second big opening of said second big pouch;

said second peripheral section of said lower sheet of each of said second big and second smaller pouches being connected to one another, said second smaller pouch being movable from a first position to a second position in which in said first position, said second smaller opening of said second smaller pouch is located immediately within said second big opening of said second big pouch and said second smaller pouch is generally located within said second big pouch, and in said second position, said second peripheral section of said lower surface of said second smaller pouch overlies said second big opening, and said second smaller pouch is generally located outside of said second big pouch.

12. A device as recited in claim 10, wherein:
said first and second sheets of said first big and first smaller pouches are transparent.

13. A device as recited in claim 10, wherein:
said first and second peripheral sections of said first smaller pouch are generally first smaller than said peripheral sections of said large pouch so that said first smaller pouch can lie flat within said large pouch when said pouches are in said first position.

14. A drape as recited in claim 10, wherein:
said first big pouch includes a drainage port.

15. A drape as recited in claim 10, further comprising:
means for releasably attaching said second peripheral sections of said upper surfaces of said first big and first smaller pouches to one another.

16. A drape as recited in claim 10, further comprising:
means for releasably attaching said second peripheral sections of said upper and lower surfaces of said first smaller pouch to one another.

17. A drape as recited in claim 16, further comprising:
means for releasably attaching said second peripheral sections of said upper and lower surfaces of said first smaller pouch to one another.

18. A drape as recited in claim 17, further comprising:
means for stiffening said second peripheral sections of said upper sheet of at least one of said first big and first smaller pouches.

19. A drape as recited in claim 10, further comprising:
means for attaching said second peripheral section of said lower sheet of said first big pouch to a surface adjacent a patient's appendage.

* * * * *